(12) United States Patent
Göllner et al.

(10) Patent No.: US 9,486,565 B2
(45) Date of Patent: Nov. 8, 2016

(54) CONNECTING ELEMENT FOR MOUNTING A BLOOD PUMP OR A CANNULA ON A HEART

(71) Applicant: Berlin Heart GmbH, Berlin (DE)

(72) Inventors: Manfred Göllner, Berlin (DE); Ulrich Tim Opfermann, Berlin (DE); Peter Nüsser, Kleinmachnow (DE); Andreas Arndt, Berlin (DE); Felix Von Winterfeld, Berlin (DE)

(73) Assignee: Berlin Heart GmbH, Berlin (DE)

( * ) Notice: Subject to any disclaimer, the term of this patent is extended or adjusted under 35 U.S.C. 154(b) by 0 days.

(21) Appl. No.: 14/354,922

(22) PCT Filed: Oct. 31, 2012

(86) PCT No.: PCT/EP2012/071543
§ 371 (c)(1),
(2) Date: Apr. 28, 2014

(87) PCT Pub. No.: WO2013/064529
PCT Pub. Date: May 10, 2013

(65) Prior Publication Data
US 2014/0288355 A1    Sep. 25, 2014

(30) Foreign Application Priority Data
Oct. 31, 2011   (DE) .................. 10 2011 117 892

(51) Int. Cl.
*A61M 1/00* (2006.01)
*A61M 1/10* (2006.01)
*A61M 1/12* (2006.01)

(52) U.S. Cl.
CPC .......... *A61M 1/1008* (2014.02); *A61M 1/1098* (2014.02); *A61M 1/12* (2013.01); *A61M 1/122* (2014.02)

(58) Field of Classification Search
CPC .... A61M 1/10; A61M 1/1008; A61M 1/122; A61M 1/12
USPC ....................................... 600/16–18
See application file for complete search history.

(56) References Cited

U.S. PATENT DOCUMENTS

| | | | |
|---|---|---|---|
| 2002/0045846 A1 | 4/2002 | Kaplon et al. | |
| 2003/0078592 A1 | 4/2003 | Heilman et al. | |
| 2006/0074484 A1 | 4/2006 | Huber | |

(Continued)

FOREIGN PATENT DOCUMENTS

| | | |
|---|---|---|
| CN | 87107936 A | 7/1988 |
| DE | 3218242 A1 | 11/1983 |

(Continued)

OTHER PUBLICATIONS

International Search Report dated Feb. 1, 2013, International Patent Application No. PCT/EP2012/071543, pp. 1-10, European Patent Office, Rijswijk, the Netherlands.

*Primary Examiner* — Scott Getzow
(74) *Attorney, Agent, or Firm* — Brinks Gilson & Lione

(57) ABSTRACT

A connecting element for connecting a blood pump or a cannula to a heart, the connecting element including a sealing element, which is designed to at least temporarily close an opening formed in the cardiac wall and to be opened via insertion of a preferably cylindrical object in the direction of an axis of the opening.

9 Claims, 5 Drawing Sheets

(56) References Cited

U.S. PATENT DOCUMENTS

| | | |
|---|---|---|
| 2009/0062844 A1 | 3/2009 | Tekulve et al. |
| 2010/0030246 A1 | 2/2010 | Pavenik et al. |
| 2010/0161040 A1 | 6/2010 | Braido et al. |
| 2011/0118766 A1 | 5/2011 | Reichenbach et al. |

FOREIGN PATENT DOCUMENTS

| | | |
|---|---|---|
| DE | 10249371 A1 | 4/2003 |
| EP | 0 273 714 A2 | 7/1988 |
| WO | WO 2011/060386 A2 | 5/2011 |
| WO | WO 2011/060386 A9 | 7/2011 |
| WO | WO 2011/060386 A3 | 12/2011 |

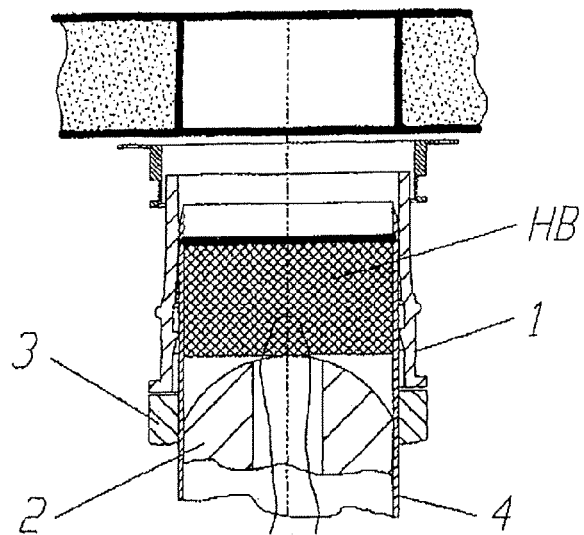
Fig. 8
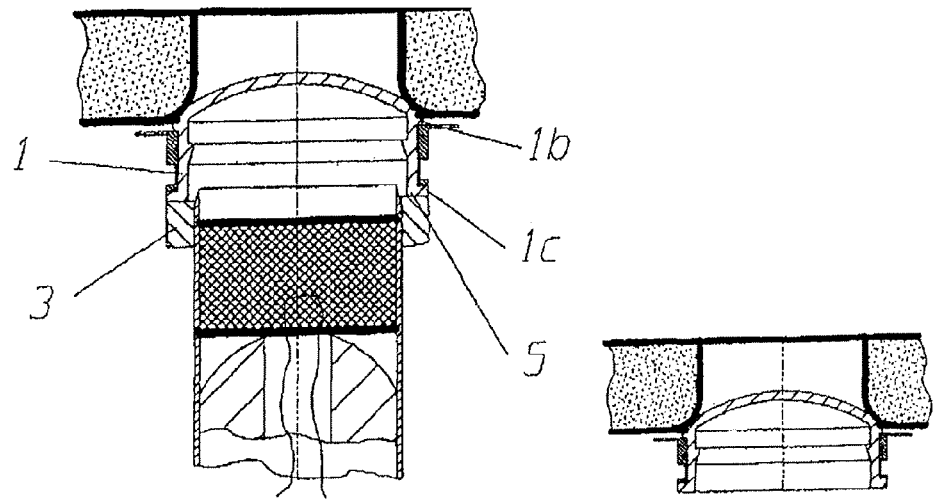
Fig. 9
Fig. 10

CONNECTING ELEMENT FOR MOUNTING A BLOOD PUMP OR A CANNULA ON A HEART

CROSS-REFERENCE TO RELATED APPLICATIONS

This application is a 371 nationalization of PCT/EP2012/071543, entitled "CONNECTING ELEMENT FOR MOUNTING A BLOOD PUMP OR A CANNULA ON A HEART," having an international filing date of Oct. 31, 2012, the entire contents of which are hereby incorporated by reference, which in turn claims priority to German patent application 102011117892.2 filed on Oct. 31, 2011, entitled "VERBINDUNGSELEMENT ZUM MONTIEREN EINER BLUTPUMPE ODER EINER KANüLE AN EINEM HERZEN," the entire contents of which are hereby incorporated by reference.

BACKGROUND

The invention relates to a connecting element for mounting a blood pump or a cannula on a heart, and a system for mounting such a connecting element on the heart.

In the implantation of heart assist systems in particular, inserting a so-called inlet cannula or the inlet connecting piece of an implantable blood pump into the heart through a previously formed opening is problematic. If the implantation will be performed without the use of a heart-lung machine, the heart continues to beat during these manipulations, and therefore blood can freely flow out during the period after the opening is formed and before the cannula/pump is inserted if makeshift sealing measures are not implemented (sealing using thumb pressure is common). The makeshift sealing measures must be carried out very quickly, however. The blood loss cannot be perfectly prevented and increases in the period between formation of the opening and insertion of the cannula.

The problem is therefore that of closing the opening in the heart after it is formed and until the cannula/pump is inserted, thereby ensuring that problems do not occur due to a relatively long time period between formation of the opening and insertion.

SUMMARY

According to the invention, a connecting element for an implantable blood pump or a cannula, which can be attached on the heart, contains a sealing element, which can be opened via axial insertion of a cylindrical object, for example, but which otherwise tightly closes an opening in the cardiac wall formed under the connecting element.

By way of such a preferably valve-like sealing element, an opening formed in the cardiac wall is reliably sealed for the time period between formation of the opening and attachment of the blood pump or cannula. As a result, blood loss is reliably reduced independently of the working speed of the operating surgeon.

The connecting element can comprise a suture ring, which can be sutured with the cardiac wall. After the blood pump or cannula is attached, the suture ring can seal the connection between the blood pump or cannula and the heart and hold the cannula or the blood pump against the heart. The connecting element can also be embodied as an anchoring element having any other type of design.

In order to obtain the best possible sealing effect between the suture ring and the pump connector, the suture ring can be made, on the inner curvature thereof, of a soft sealing material such as velour or a velour-silicone combination, for example.

The radially outward part of the suture ring can be made of a material that is highly resistant to mechanical deformation, such as titanium or surgical steel, in order to prevent or limit deformability of the suture ring during operation and therefore support of the sealing properties of the inner soft curvature against the blood pump and the cannula as described above.

In addition, a connector ring can be provided, which is used to connect the sealing element to the suture ring. The connector ring can be made of a rigid material in order to obtain the most reliable connection possible to the sealing element. The connector ring can be designed to be connected to the suture ring via bonding or suturing.

The connector ring and/or the sealing element can comprise at least one detent element, by way of which the sealing element can be locked with the connector ring. Alternatively or additionally, other connections, such as positive, non-positive or bonded connections, can be provided between the connector ring and the sealing element. For example, the connector ring can be bonded with the sealing element. The sealing element can also be integral with the connector ring.

In one exemplary embodiment, the sealing element comprises a plurality of freely openable subregions (also referred to as sectors), which have a convex side and a concave side and can be flexible. The freely openable subregions can be designed, in particular, such that they are pressure-stable with respect to pressure on the convex side, while they can be pressed open from the concave side. As a result, the blood pressure that prevails in the beating heart does not cause the sealing element to leak and even induces the sealing element to close more tightly, while the sealing element can be easily opened from the concave side, for example via insertion of a connector and/or inflow cannula of a blood pump.

The related sealing mechanism can be designed to be handled with one hand in order to simplify implantation using minimally invasive, sternum-sparing surgical techniques. This can be solved in a design-related manner using a spring element, for example, which holds a sealing element in the closed home position and can be moved into the opened position by the user, preferably using one hand. If the sealing element is released after the cutting tool has been positioned and the punch opening has been created in the cardiac wall, the sealing mechanism automatically returns to the closed home position by way of the restoring forces of the spring element. The surgeon therefore has his hands free to install the pump, and the surgical site is blood-free.

Alternatively, the sealing mechanism comprising the spring element can be actively opened simply by inserting the punching tool and/or the pump inflow cannula.

It should also be noted that it is not necessary for the sealing element to be handled directly by a user using one hand; instead, it is also possible (in the case of deeper surgical sites) for the user to work outside the body using a further auxiliary element for extension if the spatial conditions prevent work from being performed entirely by the human hand.

In one embodiment, the sealing element comprises a plurality of film layers. Each of the film layers can comprise two films, which are in contact with one another along one edge. The edges of adjacent film layers can extend at an angle relative to one another, and therefore blood emerging from the heart along one edge of a first film layer is held back by the next film layer. Basically, the number of film layers can be freely selected. A larger number of film layers results in an improved sealing effect, although this makes it difficult to subsequently open the sealing element via insertion of a cannula or a connector of a blood pump. The use of two film layers has proven to be a particularly suitable compromise between sealing effect and flexibility. The film layers can be incorporated or incorporable in the connector ring, for example.

In addition to the connecting element, the invention relates to a system for attaching a connecting element on a heart. The system comprises a connecting element of the previously described type and a tool for punching an opening in the heart. The tool comprises a first component and a blade. The first component and the blade are displaceable in the longitudinal direction of the tool relative to one another and relative to the rest of the tool. The sealing element and the tool are designed such that the sealing element can be disposed in a front region of the tool. The sealing element can be slid upward via displacement of the first component, which can be embodied as a blade guard, for example. Next, the blade can be slid through the sealing element without damaging it.

In addition to the first component and the blade, the tool can also comprise a sliding element. This can be a contact surface for the sealing element. The sliding element can be displaceable in the longitudinal direction of the tool, thereby permitting the sealing element to be pushed into the connector ring using the sliding element. This is particularly advantageous when the sealing element and/or the connector ring comprise a detent element and can be locked to one another.

BRIEF DESCRIPTION OF DRAWINGS

Exemplary embodiments of the connecting element and the system are explained in greater detail with reference to the figures and are described in terms of functionality. Shown are:

FIG. 8 shows the tool depicted in FIG. 3 having the sealing element depicted in FIG. 4 mounted thereon, in a sectional view after the opening is formed in the cardiac wall and before the sealing element becomes locked, FIG. 9 shows the tool depicted in FIG. 3 having the sealing element depicted in FIG. 4 mounted thereon, in a sectional view after the opening is formed in the cardiac wall and after the sealing element is locked, FIG. 10 shows a sectional view of the locked sealing element depicted in FIG. 4.

DETAILED DESCRIPTION

Figure 1:
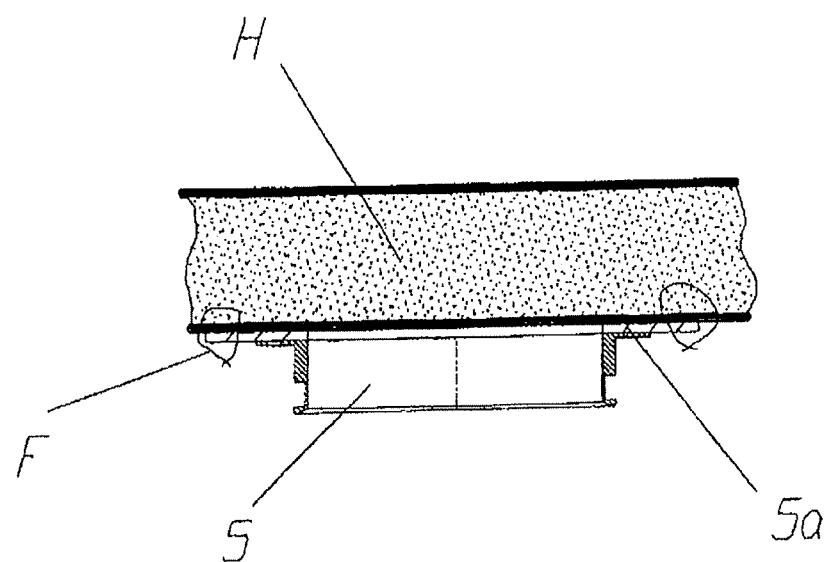
FIG. 1 shows a sectional view of a suture ring attached to a cardiac wall, comprising a connector ring mounted thereon.

As shown in FIG. 1, a suture ring 5*a*, which is made of a soft sealing material such as velour or a velour-silicone combination, for example, is sutured to the heart H using thread F before the opening is formed. The purpose of the suture ring is to hold the cannula/pump against the heart and seal the heart and the pump with respect to one another.

The suture ring is fixedly connected to a rigid connector ring 5, wherein the connection can be in the form of an adhesive connection and/or a seam.

To ensure clarity, the illustrations that follow only show the connector ring and not the suture ring.

Figure 2:
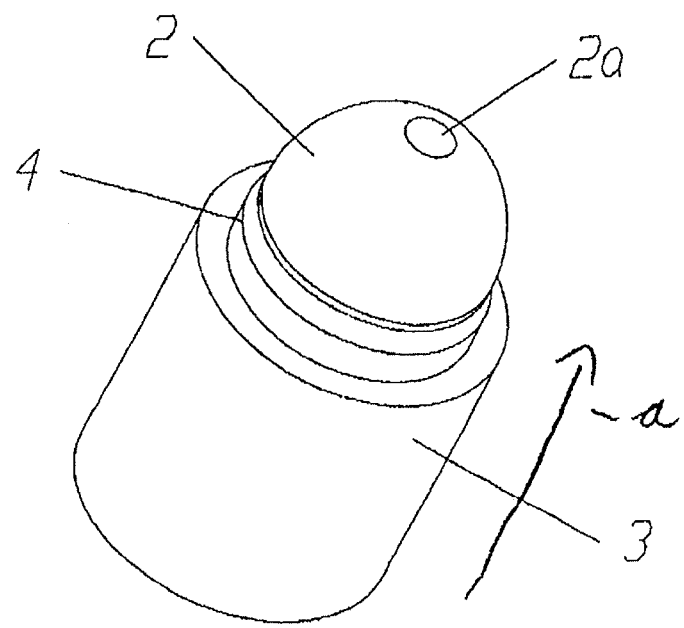
FIG. 2 shows a perspective view of a tool for forming openings in hearts, at an angle from the front.
Figure 3:
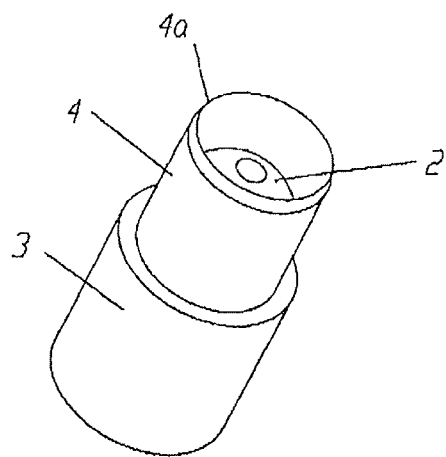
FIG. 3 shows the tool depicted in FIG. 2 with the blade slid forward.

A special tool, which is shown in FIG. 2, is used to form an opening in the heart. This comprises a blade guard 2, the blade 4 and a sliding element 3. The parts can move axially (i.e. in the direction a) relative to one another. The blade guard has a central opening for the routing therethrough of a thread, for example, or any other type of aid for captively holding the slug produced when the opening is formed. In particular, the blade can be slid forward past the blade guard, as shown in FIG. 3, thereby cutting an opening in the heart by way of the blade edge 4*a*.

Figure 4:
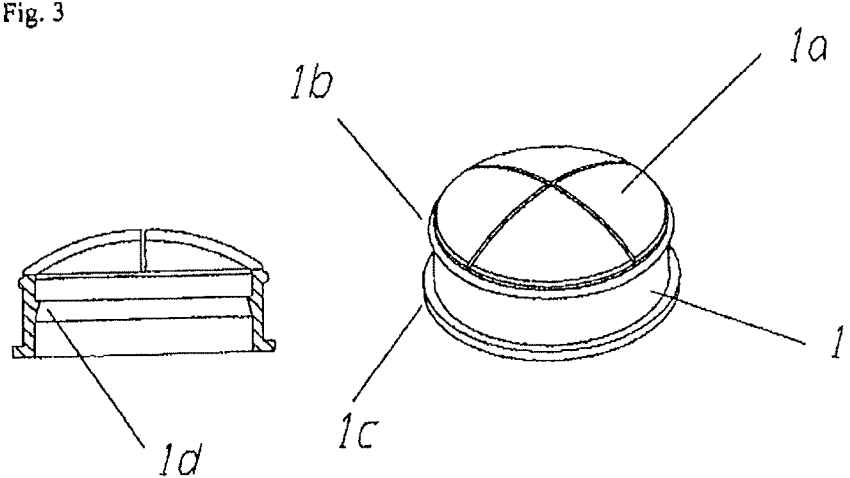
FIG. 4 shows a sectional view and a perspective view of an embodiment of a sealing element.

A valve ring 1 made of soft elastic material (silicone, in particular) can be placed onto this tool. This comprises, for example, at least three freely openable and deformable sectors 1*a*, which are formed via slits in the ring. In FIG. 4, the valve ring 1 is shown having four sectors 1*a*, although only three sectors or more than four sectors could be provided. The valve ring is further equipped with the collar 1*b* and the collar 1*c* and a sealing lip 1*d*. When the sectors are not folded open and are undeformed, they form a dome, which is pressure-stable and impenetrable (in accordance with the requirements) on the convex side. Instead of a dome, it is also possible to use so-called tricuspid flaps, which are used in artificial heart valves.

Figure 5:
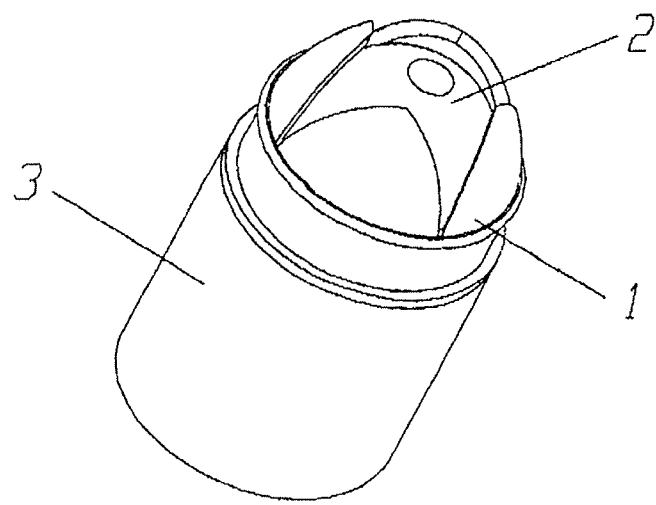
FIG. 5 shows the tool depicted in FIG. 3 having the sealing element depicted in FIG. 4 mounted thereon.

The sectors of the valve ring can be pressed open and deformed by way of the blade guard (with the blade retracted), as shown in FIG. 5.

Figure 6:
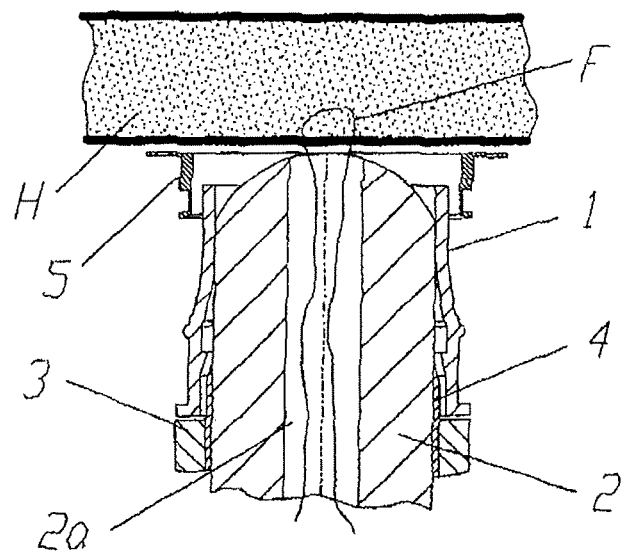
FIG. 6 shows the tool depicted in FIG. 3 having the sealing element depicted in FIG. 4 mounted thereon, in a sectional view before the opening is formed in the cardiac wall.

The tool, with the valve ring fully folded open, is inserted into the connector ring (which is connected to the not-shown suture ring). A thread F, which was previously sewn through the heart, is routed through the bore 2*a* of the blade guard, as shown in FIG. 6.

Figure 7:
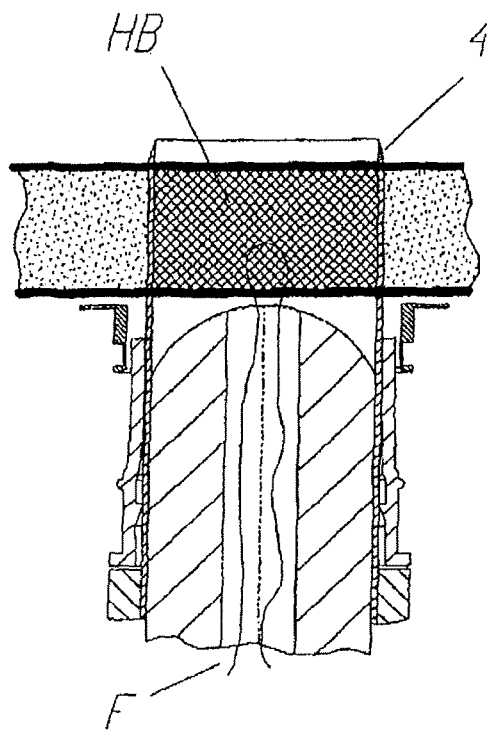
FIG. 7 shows the tool depicted in FIG. 3 having the sealing element depicted in FIG. 4 mounted thereon, in a sectional view while the opening is being formed in the cardiac wall.

When the blade is slid forward, the slug HB is cut out of the cardiac wall, wherein the slug is held steady by pulling on the thread. FIG. 7 shows the tool comprising the sealing element at this point of use.

The blade, the slug (with thread) and the blade guard can be retracted, wherein a brief (acceptable) leak forms through the gap between the valve ring sectors and the connector ring. The tool comprising the sealing element is shown in FIG. 8 at this point of retraction.

The valve ring 1 can be slid into the connector ring 5 using the sliding element 3, wherein the collars 1*b* and 1*c* fix the position. The sectors of the valve ring close and seal the opening in the heart. The seal integrity with respect to the tool is maintained since the slug rests against the blade. This situation is depicted in FIG. 9. The closed sealing element is shown in FIG. 10. The tool can now be removed.

Figure 11:
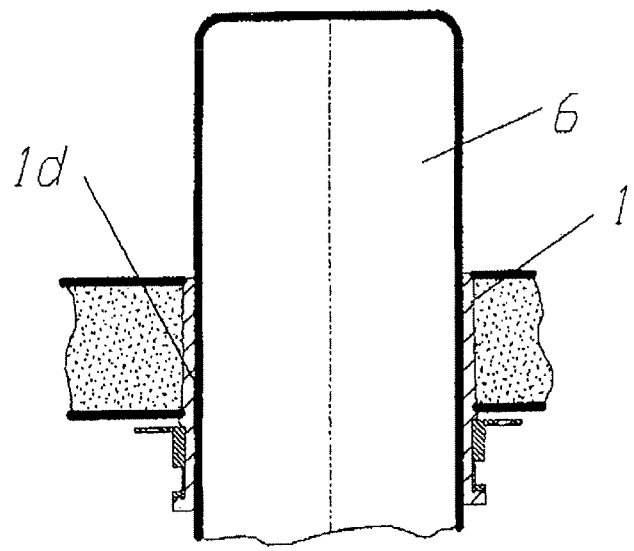
FIG. 11 shows a sectional view of the locked sealing element depicted in FIG. 4 as a pump or cannula is inserted.

When the pump/cannula 6 is inserted, the sectors of the valve ring are opened once more. The pump is connected to the connector ring via means, which are not shown. The pump is sealed with respect to the connector ring at the sealing lip 1d of the valve ring. The sealing element, with pump/cannula inserted, is shown in FIG. 11.

To prevent the sectors of the valve ring from lying against the walls of the opening in the heart, the connector ring can be designed to be higher, thereby enabling the sectors to fold open within the connector ring.

Another way to implement a suture ring valve is to equip the connector ring with, for example, four tensioned films (8a, 8b, 9a, 9b) made of thin elastic material (e.g. silicone), the adjoining edges BK of which extend radially, wherein two edges are offset by 90° in each case. Such an exemplary embodiment of a sealing element is shown in FIG. 12.

The films are fastened to the connector ring using a clamping ring 7. When a rounded cylindrical object (the aforementioned tool or pump/cannula) is inserted axially, the films are stretched, and therefore the adjoining edges thereof deform, expand and lie closely against the cylindrical surface of the object inserted through the slits.

According to a further aspect of the invention, a connecting element for an implantable blood pump or a cannula, which is attached at the heart (as usual), contains a sealing element, which can be opened via axial insertion of a cylindrical object, but which otherwise tightly closes an opening in the cardiac wall formed under the connecting element.

Figure 12:
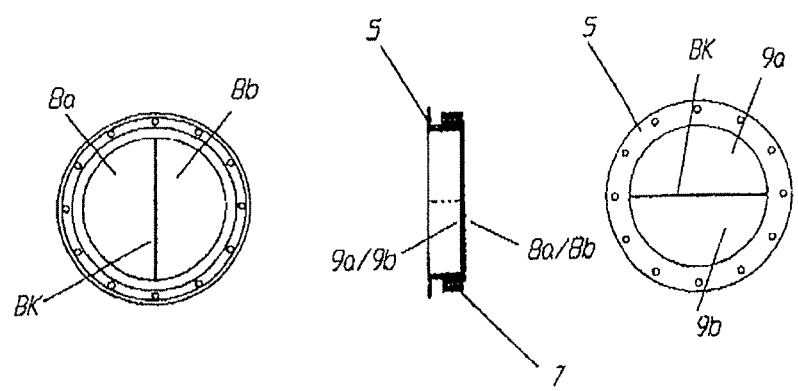
FIG. 12 shows a back view, a sectional view and a front view of an alternative embodiment of a sealing element.

The sealing element shown in FIG. 12 therefore comprises a passage channel and self-closing closing elements in the form of the tensioned films 8a, 8b, 9a and 9b. The sealing element shown there can be opened by inserting an object (e.g. the pump/cannula 6) into the passage channel completely or at least partially, thereby establishing a fluid connection between opposite ends of the passage channel. FIG. 11 further shows that the opposite ends of the passage channel formed by the sealing element are aligned in the opened state of the sealing element.

The sealing element in FIG. 4 also comprises a passage channel and closing elements for the repeated opening and closing of the passage channel, wherein the closing elements can be formed by the sectors 1a, which are fixedly connected to the valve ring 1. In the arrangement of the sealing element shown in FIG. 10, a pressure difference of approximately 100 mbar, for example, exists between the ventricle (at the top in FIG. 10) and the outer side of the heart where the sealing element is attached on the cardiac muscle, thereby forcing the sectors 1a into a closed position and closing the passage channel.

The invention claimed is:

1. A system comprising:
   a connecting element for connecting a blood pump or a cannula to a heart, the connecting element comprising a sealing element designed to at least temporarily close an opening formed in a cardiac wall of the heart and to be opened via insertion of a cylindrical object in the direction of an axis of the opening, and comprising an anchoring element for permanent attachment of the connecting element on a cardiac muscle of the heart, wherein the connecting element further comprises a connector ring for connection to at least one of the heart or a suture ring; and
   a tool for forming the opening in the heart, wherein the tool comprises a first component and at least one blade, which are displaceable in a longitudinal direction of the tool relative to one another and relative to the rest of the tool, and wherein at least the sealing element of the connecting element is disposable in a front region of the tool for forming the opening in the heart, in such a way that the sealing element of the connecting element is opened when pressed by the first component of the tool and, subsequently, permits the blade of the tool for forming the opening in the heart to pass through the sealing element, wherein the tool for forming the opening in the heart comprises a sliding element, which forms a contact surface for the sealing element and is displaceable in the longitudinal direction of the tool in order to push the sealing element into the connector ring.

2. The system of claim 1, wherein the connecting element comprises further comprising the suture ring to be sutured with the heart.

3. The system of 1, wherein at least one of the sealing element or the connector ring comprise at least one detent element, wherein the sealing element can be locked with the connector ring by way of the detent element.

4. The system of claim 1, wherein the sealing element comprises a passage channel and at least one self-closing closing element for the repeated opening and closing of the passage channel, wherein the closing element is designed to be opened via insertion of an object into the passage channel.

5. The system of claim 1, wherein the sealing element comprises a passage channel and a closing element for the repeated opening and closing of the passage channel, wherein the closing element is designed to close the passage channel when a pressure difference exists along a specified direction of the passage channel.

6. The system of claim 1, wherein the sealing element comprises a plurality of freely openable subregions, which have a convex side and a concave side such that the sealing element remains closed when pressure is applied from the direction of the convex side and opens when pressure is applied from the direction of the concave side.

7. The system of claim 1, wherein the sealing element comprises a plurality of film layers, each of which has two films, which adjoin one another along edges, wherein the edges of various film layers extend at a right angle relative to one another.

8. A system comprising:
   a connecting element comprising a sealing element configured to at least temporarily close an opening formed in a cardiac wall of a heart, the sealing element further configured to be opened via insertion of an object in a direction of an axis of the opening, the connecting element further comprising an anchoring element configured to attach the connecting element to a cardiac muscle of the heart, wherein the connecting element further comprises a connector ring; and
   a tool for forming the opening in the heart, wherein the tool for forming the opening in the heart comprises a first component and at least one blade, which are displaceable in a longitudinal direction of the tool relative to one another and relative to the rest of the tool, and wherein at least the sealing element of the connecting element is disposable in a front region of the tool in such a way that the sealing element of the connecting element is opened when pressed by the first component of the tool and, subsequently, permits the at least one blade of the tool to pass through the sealing element, wherein the tool for forming the opening in the heart comprises a sliding element that forms a contact surface for the sealing element and is displaceable in the longitudinal direction of the tool in order to push the sealing element into the connector ring.

9. The system of claim 8, wherein the first component includes a blade guard.

* * * * *